(12) United States Patent
Khadtare et al.

(10) Patent No.: US 12,208,070 B2
(45) Date of Patent: Jan. 28, 2025

(54) COMPOSITIONS CONTAINING DOFETILIDE AND MEXILETINE AND USES THEREOF

(71) Applicant: FB-HRS, LLC, Philadelphia, PA (US)

(72) Inventors: Nikhil Khadtare, Spring City, PA (US); Aruna Murty, Newtown, PA (US); Qun Liu, Skillman, NJ (US)

(73) Assignee: FB-HRS, LLC, Philadelphia, PA (US)

( * ) Notice: Subject to any disclaimer, the term of this patent is extended or adjusted under 35 U.S.C. 154(b) by 0 days.

(21) Appl. No.: 18/317,654

(22) Filed: May 15, 2023

(65) Prior Publication Data

US 2023/0381123 A1 Nov. 30, 2023

Related U.S. Application Data

(63) Continuation of application No. PCT/US2021/072467, filed on Nov. 17, 2021.

(60) Provisional application No. 63/115,258, filed on Nov. 18, 2020.

(51) Int. Cl.
| | |
|---|---|
| *A61K 31/18* | (2006.01) |
| *A61K 9/48* | (2006.01) |
| *A61K 31/138* | (2006.01) |
| *A61K 47/02* | (2006.01) |
| *A61K 47/38* | (2006.01) |

(52) U.S. Cl.
CPC ............ *A61K 31/18* (2013.01); *A61K 9/4825* (2013.01); *A61K 31/138* (2013.01); *A61K 47/02* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 3,659,019 | A * | 4/1972 | Koppe | F41J 11/02 564/259 |
| 6,805,881 | B1 * | 10/2004 | Kanikanti | A61P 9/10 424/458 |
| 9,597,302 | B1 | 3/2017 | Yan et al. | |
| 2002/0098232 | A1 * | 7/2002 | Midha | A61K 9/209 424/457 |
| 2006/0024352 | A1 * | 2/2006 | Poxon | A23L 33/15 514/169 |
| 2006/0246134 | A1 * | 11/2006 | Venkatesh | A61P 25/18 424/469 |
| 2009/0253801 | A1 | 10/2009 | Shah et al. | |
| 2010/0104637 | A1 * | 4/2010 | Qiu | A61K 9/2018 424/464 |
| 2011/0071135 | A1 * | 3/2011 | Chase | A61K 9/2054 514/319 |
| 2017/0266115 | A1 * | 9/2017 | Appel | A61K 9/5078 |
| 2019/0240158 | A1 * | 8/2019 | Yenkar | A61K 31/18 |

FOREIGN PATENT DOCUMENTS

| | | |
|---|---|---|
| CN | 101032462 A | 9/2007 |
| WO | 2012010977 A2 | 1/2012 |

OTHER PUBLICATIONS

Guo, Yutao et al. "Prevalence, incidence, and lifetime risk of atrial fibrillation in China: new insights into the global burden of atrial fibrillation," Chest vol. 147, issue 1 (2015) pp. 109-119.
Chei, Choy-Lye et al. "Prevalence and Risk Factors of Atrial Fibrillation in Chinese Elderly: Results from the Chinese Longitudinal Healthy Longevity Survey," Chinese Medical Journal, vol. 128, issue 18 (Sep. 20, 2015) pp. 2426-2432.
Chugh, Sumeet S. et al. "Worldwide epidemiology of atrial fibrillation: A Global Burden of Disease 2010 Study," Circulation, vol. 129, issue 8 (Feb. 25, 2014) pp. 837-847.
Colilla, Susan et al. "Estimates of current and future incidence and prevalence of atrial fibrillation in the U.S. adult population," American Journal of Cardiology, vol. 112, issue 8 (Oct. 15, 2013) pp. 1142-1147.
Suttorp, Maarten J., et al. "Efficacy and safety of a new selective class III antiarrhythmic agent Dofetilide in paroxysmal atrial fibrillation or atrial flutter," American Journal of Cardiology, vol. 69, issue 4 (Feb. 1, 1992) pp. 417-419.
Rasmussen, H. S., et al. "Dofetilide, A Novel Class III Antiarrhythmic Agent," Journal of Cardiovascular Pharmacology, vol. 20, suppl. 2 (1992) pp. S96-S105.
Zimetbaum, Peter "Antiarrhythmic drug therapy for atrial fibrillation," Circulation, vol. 125, issue 5 (2012) pp. 381-389.
Qin, Dingxin et al. "Comparative effectiveness of antiarrhythmic drugs for rhythm control of atrial fibrillation," Journal of Cardiology, vol. 67, issue 5 (2016) pp. 471-476.
Aktas, Mehmet K., et al. "Dofetilide-induced long QT and torsades de pointes," Annals of Noninvasive Electrocardiology, vol. 12, issue 3 (Jul. 2007) pp. 197-202.
Qi, Datun et al. "Heterogeneous distribution of INa-L determines interregional differences in rate adaptation of repolarization," Heart Rhythm, vol. 12, issue 6 (Jun. 2015) pp. 1295-1303.
Badri, Marwan et al. "Mexiletine Prevents Recurrent Torsades de Pointes in Acquired Long QT Syndrome Refractory to Conventional Measures," JACC: Clinical Electrophysiology, vol. 1, issue 4 (Aug. 2015) pp. 315-322.
Yan, Gan-Xin et al. "Phase 2 early afterdepolarization as a trigger of polymorphic ventricular tachycardia in acquired long-QT syndrome: Direct evidence from intracellular recordings in the intact left ventricular wall," Circulation, vol. 103 (Jun. 12, 2001) pp. 2851-2856.

(Continued)

*Primary Examiner* — Katherine Peebles

(74) *Attorney, Agent, or Firm* — Ice Miller LLP

(57) ABSTRACT

Described are pharmaceutical compositions in fixed dose combinations containing: a) a dofetilide component; and b) a mexiletine component; wherein the dofetilide component and the mexiletine component are physically separated from each other, along with methods of treating or preventing atrial fibrillation or a symptom associated therewith in a subject in need thereof by administering to the subject such a pharmaceutical composition and methods of preparing such fixed dose combination products.

14 Claims, No Drawings

(56) References Cited

OTHER PUBLICATIONS

Talbot, R. G., et al. "Treatment of ventricular arrhythmias with mexiletine (Ko 1173)," Lancet (Aug. 25, 1973) pp. 399-404.

Campbell, N. P. S. et al. "Mexiletine (Ko 1173) in the management of ventricular dysrhythmias," Lancet (Aug. 25, 1973) pp. 404-407.

January, Craig T. et al. "2014 AHA/ACC/HRS guideline for the management of patients with atrial fibrillation: executive summary: a report of the American College of Cardiology/American Heart Association Task Force on practice guidelines and the Heart Rhythm Society," Circulation, vol. 130, issue 23 (Mar. 28, 2014) pp. 2071-2104.

Gupta, Yogendra Kumar et al. "Fixed dose drug combinations: Issues and challenges in India," Indian Journal of Pharmacology, vol. 48, issue 4 (2016) pp. 347-349.

International Search Report (Form PCT/ISA/210) for International Patent Application No. PCT/US2021/072467, issued from the International Searching Authority, date of mailing Jun. 9, 2022, 3 pages.

Written Opinion of the International Searching Authority (Form PCT/ISA/237) for International Patent Application No. PCT/US2021/072467, issued from the International Searching Authority, date of mailing Jun. 9, 2022, 6 pages.

Miller J M, Zipes D P. Therapy for Cardiac Arrhythmias. In: Mann D. L., Zipes D. P., Libby P., Bonow J. O. (eds) Braunwald's Heart Disease: A Textbook of Cardiovascular Medicine. Elsevier Publisher. 2014: 693.

Muhammad Abubakar Shakir, et al, "Combination Therapy with Dofetilide and Mexiletine for Atrial Fibrillation: Increased Efficacy and Decreased QT Interaval Prolongation," ACC.20, World Congress of Cardiology, JACC Mar. 24, 2020, vol. 75, Issue 11 (1 page).

Muhammad Shakir, et al, "Mexiletine: A Treatment for all Cause Acquired QT Interval Prolongation," ACC.20, World Congress of Cardiology, JACC Mar. 24, 2020, vol. 75, Issue 11 (1 pages).

Farah Olleik, et al, "Mexiletine: Antiarrythmic mechanisms, emerging clinical applications and mortality," Pacing Clinical Electrophysiol. vol. 1-9, 2023.

\* cited by examiner

COMPOSITIONS CONTAINING DOFETILIDE AND MEXILETINE AND USES THEREOF

CROSS-REFERENCE TO RELATED APPLICATION

This application is a continuation of International Application No. PCT/US2021/072467, filed on Nov. 17, 2021, which published in the English language on May 11, 2023, under International Publication No. WO2023/080910, which claims priority to U.S. Provisional Application No. 63/115,258, filed on Nov. 18, 2020. Each disclosure is incorporated herein by reference in its entirety.

BACKGROUND OF THE INVENTION

Atrial fibrillation is the most common abnormal heart rhythm affecting approximately 5.2 million people in United States, more than 10 million in China[1,2] and 33 million world-wide.[3] Despite improvements in primary and secondary prevention of coronary artery disease, and effective treatment of hypertension and other heart diseases, the prevalence of atrial fibrillation continues to rise. The rise in atrial fibrillation may, at least in part, be due to the longer average life span of humans. It is projected that atrial fibrillation prevalence will increase to 12.1 million cases in 2030 in the US.[4] Atrial fibrillation predisposes patients, particularly elders, to a higher risk for stroke, heart failure, and death. About 35% of all strokes in the U.S. annually are attributed to atrial fibrillation.

One of the important treatment approaches for atrial fibrillation is to restore and maintain normal heart rhythm. Currently, there are two major clinical approaches for this treatment: (1) drug therapy; and (2) radiofrequency ablation. Both approaches have advantages and disadvantages, and both are insufficient to eliminate atrial fibrillation.

There is a higher reoccurrence rate of atrial fibrillation when patients are treated with drug therapy than radiofrequency ablation due to relatively poor efficacy and worse incidence of adverse effects of drugs for the management of atrial fibrillation. Although dofetilide has been used for the treatment of atrial fibrillation for more than 20 years,[5,6] its annual prescription represents only 2% of antiarrhythmic drug prescription (versus another antiarrhythmic drug amiodarone that represents 45%) among only a few antiarrhythmic drugs available in the market.[7] In addition, dofetilide has not been approved for use in Europe and China. The major reasons for insignificant use of dofetilide by clinicians include: its relatively suboptimal efficacy;[8] a risk of QT prolongation leading to life-threatening ventricular arrhythmias termed torsade de points (TdP),[9] as a result, a 3-day mandatory in-hospital loading period required by the US FDA; and experience is needed when using the drug, so that adverse events associated with overloading of dofetilide into the system are avoided or minimized.

There remains a need for novel, effective, safe methods and pharmaceutical compositions for treating or preventing atrial fibrillation and related symptoms. Specifically, there is a need for novel methods and pharmaceutical compositions that provide more effective prevention and/or treatment of atrial fibrillation in patients in need thereof, while reducing the risk of adverse effects, such as incidence of TdP.

It is known that mexiletine not only is an effective suppressor of TdP via inhibition of the late sodium current, but also acts synergistically with dofetilide, an antiarrhythmic drug for the treatment of atrial fibrillation, to result in a major improvement in the treatment of atrial fibrillation, with a decreased risk of ventricular arrhythmias, such as described in U.S. Pat. No. 9,597,302, the entire contents of which are hereby incorporated herein by reference. It is suggested that combined use of dofetilide and mexiletine broadens the dose range of dofetilide (i.e., allowing higher dofetilide dose to be administered safely, resulting in higher efficacy and coverage of treatment) in the treatment of atrial fibrillation because of the synergistic effect of both drugs in suppression of atrial fibrillation and reduction of risks of ventricular proarrhythmias. This should greatly enhance capability of clinicians to treat atrial fibrillation in a conservative way rather than via invasive procedures like radiofrequency ablation because both efficacy and safety profiles of the combined use of dofetilide and mexiletine are markedly improved.

Even though combinations of dofetilide and mexiletine can be obtained by admixing such active ingredients with carriers, it is not known how to predict which of such combinations will have physicochemical properties that will render the composition suitable for pharmaceutical use. A fixed-dose combination product (FDC) contains two or more drugs combined in a fixed ratio into a single, or unit, dosage form. The terms single dosage form and unit dosage form are used herein interchangeably. The development of a specific fixed-dose combination (FDC) product that has a plurality of active pharmaceutical ingredients (APIs) with desired pharmaceutical properties is often an unpredictable task regarding, for example, the choice of APIs and non-API components in such fixed-dose form and its manufacture. If physical pharmaceutical properties, such as hygroscopicity, crystallinity, melting point, solubility, dissolution rate, and stability, can present predictability challenges in the context of single API formulations, such challenges become more accentuated in the case of single dosage forms with a plurality of APIs and other components in them because of possible reactivity within the form itself among its constituent components. Because of these liniations in what one of ordinary skill in the art would be able to expect or successfully predict regarding such properties, and the role that they play in certain aspects of the pharmaceutical industry, there still remains a need for finding formulations of certain pharmaceutical compounds that render them acceptable as pharmaceutical preparations. Pharmaceutical preparations that are based on the concomitant dosing of two or more APIs in a single dosage form are acknowledged to be advantageous and desirable, because they provide one or more benefits such as therapeutic efficacy potentiation, reduction of incidence of adverse effects, pharmacokinetic advantages, adherence and compliance improvement by burden pill reduction, individual drug dose reduction or regimen simplification, decrease of resistance development, and potential cost reduction form packaging to distribution. However, they are regarded as being difficult to develop because they can pose problems such as pharmacodynamic mismatch, pharmacokinetic mismatch, chemical incompatibilities, drug interactions, and limitations of finer dosing titration of individual ingredients. See, for example, Y.K. Gupta, et al., Fixed dose drug combinations: Issues and challenges in India, Indian J. Pharmacol. 48(4), 347-49 (2016) (setting forth generally problems with fixed dose combinations and motivations for pursing them). Various means to achieve multiple API dosing in the past have included discrete dosage forms for each API, contained in a single package, multiple APIs in one dosage form, and multiple layers of different APIs in a compressed tablet. However, compatibility of the various APIs can limit the use of such techniques.

Additionally, various excipients components commonly used in pharmaceutical compositions can interact with each other and with APIs differently to the detriment of physical and/or chemical characteristics of the combination. For example, a filler commonly used with one API may not perform well with another API or other excipients in the combination. Thus, it is increasingly difficult to formulate more than one API into a single dosage form without detrimentally impacting the properties of the fixed dose combination.

BRIEF SUMMARY OF THE INVENTION

The present invention is directed, in general, to pharmaceutical compositions containing a dofetilide component and a mexiletine component. The present invention is also directed, in general, to methods of treating or preventing atrial fibrillation using combinations of dofetilide and mexiletine in accordance with the various formulation embodiments of the present invention. Various embodiments of the present invention thus provide combined dual-active formulations of dofetilide and mexiletine in a single dosage unit, which can include immediate-release, extended release and/or modified release components.

Various embodiments of the present invention include a pharmaceutical composition in unit dosage form comprising: a) a dofetilide component; and b) a mexiletine component; wherein the dofetilide component and the mexiletine component are contained within a single dosage unit; wherein the dofetilide component comprises an effective amount of dofetilide active ingredient, and one or more pharmaceutically acceptable excipients; wherein the mexiletine component comprises an effective amount of mexiletine, and one or more pharmaceutically acceptable excipients; and wherein the dofetilide component and the mexiletine component are physically separated from each other, for example, by an inert layer coating each API containing particles and/or by incorporating each API in the form of minitablets or granules into the combination.

In various embodiments in accordance with the present invention, separating the dofetilide component and the mexiletine component from each other can comprise filling two separate compartments of a multi-compartment pharmaceutical delivery system (e.g., multicompartment capsule), one each with the dofetilide component and the mexiletine component. In various embodiments in accordance with the present invention, separating the dofetilide component and the mexiletine component from each other can comprise tableting or otherwise compounding the dofetilide component and the mexiletine component in solid forms with an inert, intervening layer or film. In various embodiments in accordance with the present invention, separating the dofetilide component and the mexiletine component from each other can comprise coating one or both of the dofetilide component and the mexiletine component. In various embodiments in accordance with the present invention, the dofetilide component and the mexiletine component can be in different states (e.g., solid and liquid) and physically separated.

Embodiment of the present invention include a pharmaceutical composition in unit dosage form comprising: a) a dofetilide component; and b) a mexiletine component; wherein the dofetilide component and the mexiletine component are contained within a capsule; wherein the dofetilide component comprises an effective amount of dofetilide active ingredient, by itself, or in conjunction with one or more pharmaceutically acceptable excipients; wherein the mexiletine component comprises an effective amount of mexiletine, by itself, or in conjunction with one or more pharmaceutically acceptable excipients; and wherein at least one of the dofetilide component and mexiletine component is compressed and coated with a polymeric film coating.

Other embodiment of the present invention include a method of treating or preventing atrial fibrillation or a symptom associated therewith in a subject in need thereof, the method comprising administering to the subject the pharmaceutical composition according to any of the formulation embodiments described herein.

In various embodiments, combined dual-active formulations of dofetilide and mexiletine can be in an immediate-release, an extended release or a modified release dosage unit. In various embodiments, mexiletine can be granulated in a blend that comprises various excipients and is formulated into tablets or pellets or granules. In various embodiments, the mexiletine and/or dofetilide can be powdered, liquid or in suspension. In various embodiments, dofetilide can be mixed in a blend that comprises various excipients and is formulated into tablets or pellets or granules. In various embodiments, one or more polymeric coats is layered over the mexiletine tablets or pellets. In various embodiments, one or more polymeric coat is layered over the dofetilide tablets or pellets. In various embodiments, the dofetilide tablets or pellets and mexiletine tablets or pellet can be contained in a capsule. In various embodiments, the pharmaceutical composition containing the dofetilide and mexiletine components exhibits content uniformity, and stability. In various embodiments, combined dual-active formulations of dofetilide and mexiletine do not develop changes such as browning and color variation.

Various embodiments of the invention relate to methods of manufacturing a pharmaceutical composition that comprises effective amounts of dofetilide and mexiletine with various excipients. Examples provided herein illustrate embodiments of such methods.

Embodiments of this invention comprise amounts of dofetilide and mexiletine illustrated by amounts such as the following:

dofetilide ranges from 0.113 μmol to 5.66 μmol, and mexiletine ranges from 0.139 mmol to 4.64 mmol;

dofetilide ranges from 50 mcg to 2500 mcg, and mexiletine is in the form of mexiletine hydrochloride that ranges from 30 mg to 1000 mg;

dofetilide in an amount from 100 mcg to 600 mcg and mexiletine in an amount from 100 mg to 500 mg mexiletine hydrochloride, such as (a) 125 mcg dofetilide with 150, 200, 250, 300, 350, 400, 450, or 500 mg mexiletine hydrochloride, (b) 250 mcg dofetilide and 150, 200, 250, 300, 350, 400, 450, or 500 mg mexiletine hydrochloride, (c) 375 mcg dofetilide and 150, 200, 250, 300, 350, 400, 450, or 500 mg mexiletine hydrochloride, (d) 500 mcg dofetilide and 150, 200, 250, 300, 350, 400, 450, 500 mg mexiletine hydrochloride;

500 mcg dofetilide and 275 mg mexiletine hydrochloride;

500 mcg dofetilide and 245 mg mexiletine hydrochloride;

dofetilide in an amount from 125 mcg to 500 mcg dofetilide and mexiletine in an amount from 160 mg to 280 mg mexiletine hydrochloride, such as 500 mcg dofetilide and 245, 250, 255, 260, 265, 270, 275 or 280 mg mexiletine hydrochloride; and dofetilide in an amount of 250 mcg or 500 mcg dofetilide and mexiletine in an amount of 165 mg or 245 mg mexiletine hydrochloride.

Further embodiments of this invention are illustrated by compositions in which dofetilide and mexiletine are present in any of the foregoing respective amounts, and such that the dofetilide component has impurities analyzed over time that satisfy at least one of the three characteristics chosen from the following (a), (b) and (c):
- (a) below quantitation limit at room temperature and less than 0.5% under 40° C./75% RH conditions one month after the pharmaceutical composition was prepared,
- (b) less than 0.8% under 40° C./75% RH conditions two months after the pharmaceutical composition was prepared, and
- (c) less than 0.3% at room temperature and less than 1% under 40° C./75% RH conditions three months after the pharmaceutical composition; and
- wherein the mexiletine component has impurities analyzed over time that satisfy at least one of the three characteristics chosen from the following (d), (e) and (f):
- (d) below quantitation limit at room temperature and under 40° C./75% RH conditions one month after the pharmaceutical composition was prepared,
- (e) below quantitation limit under 40° C./75% RH conditions two months after the pharmaceutical composition was prepared, and
- (f) below quantitation limit at room temperature and under 40° C./75% RH conditions three months after the pharmaceutical composition was prepared.

Further embodiments of this invention are illustrated by compositions in which dofetilide and mexiletine are present in any of the foregoing respective amounts, and such that the dofetilide component has impurities analyzed over time that satisfy at least one of the three characteristics chosen from the following (a), (b) and (c):
- (a) below quantitation limit at room temperature and less than 0.2% under 40° C./75% RH conditions one month after the pharmaceutical composition was prepared,
- (b) less than 0.5% under 40° C./75% RH conditions two months after the pharmaceutical composition was prepared, and
- (c) less than 0.2% at room temperature and less than 0.7% under 40° C./75% RH conditions three months after the pharmaceutical composition; and
- wherein the mexiletine component has impurities analyzed over time that satisfy at least one of the three characteristics chosen from the following (d), (e) and (f):
- (d) below quantitation limit at room temperature and under 40° C./75% RH conditions one month after the pharmaceutical composition was prepared,
- (e) below quantitation limit under 40° C./75% RH conditions two months after the pharmaceutical composition was prepared, and
- (f) below quantitation limit at room temperature and under 40° C./75% RH conditions three months after the pharmaceutical composition was prepared.

Other aspects, features and advantages of the invention will be apparent from the following disclosure, including the detailed description of the invention, illustrative embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Terms such as "at least one of [list of elements]", "at least one of [ . . . ] chosen from [lists of elements]", and analogous terms used throughout the written description and claims are meant to include anyone of a plurality of possibilities that include, but are not necessarily limited to, unless indicated otherwise, the choice of only one element in the list of elements. For example, "at least of one of A and B" is meant to include embodiments that refer only to A, embodiments that refer only to B, and embodiments that refer to A and B.

As used herein and unless indicated otherwise, the name of a compound can encompass all possibly existing isomeric forms (e.g., optical isomer, enantiomer, diastereomer, racemate or racemic mixture), esters, prodrugs, metabolite forms, pharmaceutically acceptable salts, pharmaceutically acceptable esters, pharmaceutically acceptable amides, and protected derivatives, of the compound.

As used herein, the term "subject" means any animal, preferably a mammal, most preferably a human, to whom will be or has been administered a compound or a pharmaceutical composition according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of, treatment or prevention of atrial fibrillation and symptoms associated therewith, more preferably, such a subject is an elderly human subject.

A "subject" as described herein is preferably in need of treatment or prevention of atrial fibrillation and symptoms associated therewith. Atrial fibrillation is an abnormal heart rhythm characterized by irregular and often rapid beating that commonly causes poor blood flow to the body. During atrial fibrillation, the heart's two upper chambers (the atria) beat chaotically and irregularly out of coordination with the two lower chambers (the ventricles) of the heart. Symptoms of atrial fibrillation include, for example, heart palpitations, dizziness, light-headedness, fainting, shortness of breath, chest pain, anginal chest pain, exercise intolerance, and swelling of the extremities. Although episodes of atrial fibrillation can come and go without causing symptoms, atrial fibrillation may lead to blood clots forming in the heart that may circulate to other organs and lead to blocked blood flow (ischemia). Subjects with a history of stroke, transient ischemic attack (TIA), high blood pressure, diabetes, heart failure, rheumatic fever, or a family history of atrial fibrillation can have a higher risk or predisposition to developing atrial fibrillation, or developing complications associated with already diagnosed atrial fibrillation. Thus, such subjects can be in need of prevention of atrial fibrillation, or at increased need of treatment of atrial fibrillation.

The present disclosure provides information and study protocol summaries to ascertain pharmacological features of illustrative embodiments of the invention, such as bioavailability, drug-drug interactions and effects of factors, such as food effect, and such protocols can also be used with methods known to those of ordinary skill in the art, each alone or in combination, to determine additional pharmacological features, such as therapeutically effective amounts of active ingredients. Furthermore, and as is also understood by those of ordinary skill in the art, specific dose levels for any particular subject will depend upon a variety of factors including the age, body weight, general health, sex, diet, time of administration, route of administration, rate of excretion, any additional therapeutic agents administered in combination therewith and the severity of the disease or condition being treated.

Compositions of the invention include one or more therapeutically active ingredients, prodrugs thereof, pharmaceutically acceptable salts thereof, hydrates thereof, solvates thereof and combinations thereof. Specifically, therapeutically active ingredients of present pharmaceutical compositions include dofetilide and mexiletine.

The term "dofetilide" refers to the compound N-[4-(2-{[2-(4-methanesulfonamidophenoxy)ethyl](methyl) amino}ethyl)phenyl] methanesulfonamide, having the structure of formula (I):

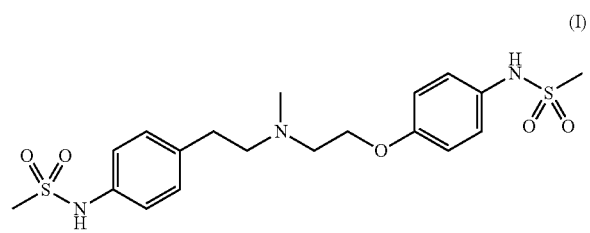

(I)

Any prodrug, pharmaceutically acceptable salt, hydrate, solvate, or combination thereof is envisaged to perform as dofetilide in embodiments of this invention, provided that appropriate conversion is made of the applicable amount when it is given by weight.

Dofetilide is distributed by Pfizer, Inc. under the tradename Tikosyn®. Dofetilide is an antiarrhythmic drug that has been in market for the treatment of atrial fibrillation for more than 20 years.[5,6] However, its efficacy is suboptimal.[8] Administration of dofetilide can also lead to adverse effects, such as an increased risk of QT prolongation, leading to the life-threatening ventricular arrhythmias, TdP triggered by R-on-T extrasystoles via a mechanism of early afterdepolarization (EAD).[12] Although it is uncommon, the risk of TdP by dofetilide can be significantly increased by many factors including hypokalemia, female gender, drug interaction, ventricular hypertrophy and renal function insufficiency. In various embodiments of the present invention, a dofetilide component with an average particle size (d90) of less than 10 μm can be used.

The term "mexiletine" refers to any of the compounds (RS)-1-(2,6-dimethylphenoxy)propan-2-amine or 2-(2-aminopropoxy)-1,3-dimethylbenzene, having the structure of formula (II) in its hydrochloride form:

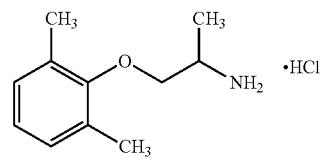

(II)

Any prodrug, pharmaceutically acceptable salt, including but not limited to mexiletine hydrochloride, hydrate, solvate, or combination thereof is envisaged to perform as mexiletine in embodiments of this invention, provided that appropriate conversion is made of the applicable amount when it is given by weight. Mexiletine is a sodium channel blocker that has been used for the treatment of documented ventricular arrhythmias, such as sustained ventricular tachycardia since the early 1970s.[13,14] It also blocks INA-L (late sodium current), which has recently been shown to be an effective treatment approach to terminate TdP in acquired LQTS (Long QT syndrome), such as LQTS acquired by the administration of dofetilide.[11] However, it is generally believed that mexiletine exerts little electrophysiological effect in atria, i.e., that it is not atria-selective. Therefore, mexiletine is not indicated for effective treatment of atrial fibrillation,[15] and it is also not included in any of the guidelines for the management of patients with atrial fibrillation by American College of Cardiology, American Heart Association and the Heart Rhythm Society.[16]

The term "pellet" refers to a formulation exhibiting a diameter of about 5.0 mm or less, that has undergone a process of compression or has been made by layering onto nonpareils or extrusion optionally followed by spheronisation or other similar known techniques.

The term "granule" refers to a pharmaceutical formulation whereby the ingredients have been mixed together in order to intimately and evenly disperse the API within some or all of the other ingredients and to increase the particle size. Well known techniques are known in the pharmaceutical industry and can be selected from wet or dry granulation.

The term "tablet" refers to coated or uncoated tablets, single layer or multiple layer tablets and any other dosage form which has undergone a process of compression or compaction in order to form a solid dosage unit. As used herein, "tablet" can include pellets or mini-tablets.

The term "milling" or "milled" as used herein refers to the application of mechanical energy to physically break down coarse particles to finer ones.

Mills employable in the present process are, for example, dry mills capable of grinding a material into ultrafine particles through a mechanical impact and/or attrition, which are called high-speed stirring mills and impact mills. Specific examples of mills are cylinder-type mills such as rotating ball mill, vibrating ball mill, tube mill, rod mill, and the like.

The term "excipient" as used herein refers to therapeutically inert, pharmaceutically acceptable ingredients that are added to a pharmaceutical formulation to act as, for example, fillers or diluents, binding agents, disintegrants, flow aids or glidants, lubricants or wetting agents. Excipients falling into these and other categories of excipients are well known in pharmaceutical formulation and manufacture.

The term "geometric blending" as used herein refers to a technique of thoroughly dispersing small amount of API with an appropriate amount of a diluent in increasing proportions which ensures uniform distribution of the API in the final blend.

The term "dry blending" as used herein refers to the mixing of dry ingredients prior to further use, as in mixtures of API, filler, or other excipients.

Pharmaceutical compositions according to embodiments of the invention are formulated for oral administration. Pharmaceutical compositions adapted for oral administration include solid forms such as pills, tablets, caplets, and hard or soft capsules (each including immediate release, timed release, and sustained release formulations) as well as lozenges and dispersible powders or granules. Pharmaceutical compositions in accordance with various embodiments of the present invention are formulated in capsules. In various embodiments, a hard capsule is used.

Pharmaceutically acceptable carriers that may be desirably utilized in the manufacture of solid oral dosage forms include such as, for example, but not limited to, inert diluents, such as calcium carbonate, sodium carbonate, lactose, calcium phosphate or sodium phosphate; granulating or disintegrating agents, such as corn starch or alginic acid; binding agents, such as starch, gelatin, or acacia; and lubricating agents such as magnesium stearate, stearic acid or talc. If desired, solid pharmaceutical compositions adapted for oral administration may further include one or more sweetening agents, flavoring agents, coloring agents, or preserving agents in order to provide attractive or palatable preparations.

The effective amount of therapeutically active ingredients to be included in a dosage form will depend upon factors, such as the patient being treated, the mode of administration and the desired delivered dose. Illustrative pharmaceutical compositions as embodiments of this invention include 50 mcg to 2500 mcg of dofetilide (in the range of 0.113 μmol to 5.66 μmol of dofetilide), and 30 mg to 600 mg of mexiletine HCl per dosage form (in the range of 0.232 mmol to 4.64 mmol of mexiletine). In further embodiments 50 mcg to 1000 mcg of dofetilide and 30 mg to 600 mg of mexiletine HCl per dosage form. Illustrative effective amounts of mexiletine HCl in embodiments of this invention are 50 mg to 1000 mg in some embodiments and 100 mg to 300 mg per dosage form in further embodiments. Examples of the effective amount of mexiletine HCl can include, but are not limited to, 30 mg, 50 mg, 80 mg, 100 mg, 200 mg, 250 mg, 300 mg, 350 mg, 400 mg, 450 mg, 500 mg, 550 mg or 600 mg per dosage form. In some embodiments, dofetilide is delivered at 250 mcg or 500 mcg and mexiletine HCl is delivered at 165 mg or 245 mg strength. In light of formulae (I) and (II) given above, it is known to one of ordinary skill in the art how to refer amounts given in mass to amounts given in moles, be it in reference to each of dofetilide and mexiletine as free compounds (molar masses of 441.56 g mol$^{-1}$ and 179.26 g mol$^{-1}$, respectively) or in the form of, for example, salts (such as mexiletine HCl with a molar mass of 215.72 g mol$^{1}$). For example, reference to 0.838 mmol of mexiletine encompasses a reference to 150 mg of mexiletine free base, and also a reference to 181 mg of mexiletine HCl.

Various embodiments of the present invention include a mexiletine component wherein mexiletine is granulated in an aqueous suspension with a binder and a microcrystalline cellulose component. Suitable binders include polyvinyl pyrrolidones, hydroxypropyl methylcelluloses ("HPMC") and starches. In various embodiments, the binder can comprise a polyvinyl pyrrolidone binder. In certain embodiments of the present invention, the polyvinyl pyrrolidone binder can include Povidone K29/32.

Various embodiments of the present invention include one or more microcrystalline cellulose components. Microcrystalline celluloses suitable for use in the various embodiments of the present invention include any pharmaceutically acceptable filler, such as, for example, but not limited to, AVICEL microcrystalline cellulose available from a number of commercial sources. Generally, suitable particle sizes for microcrystalline cellulose components which can be used in the various embodiments of the present invention are from about 50 m to about 180 m. In some embodiments, the average particle sizes are from 50 μm to about 100 m. In various embodiments of the present invention, the mexiletine component is first granulated in a formulation containing a microcrystalline cellulose component, and then subsequently blended with another microcrystalline cellulose component and other optional excipients. In some embodiments, microcrystalline cellulose components having differing average particle sizes are used. In certain embodiments the mexiletine can be granulated with a microcrystalline cellulose component having a smaller average particle size than the microcrystalline cellulose using in the subsequent blending.

In various embodiments of the invention, a mexiletine component can be prepared by granulating mexiletine with a microcrystalline cellulose in an aqueous suspension of a polyvinylpyrrolidone (PVP). In various embodiments of the invention, the granules can be dried in an oven and milled, for example using a Fitzmill comminuting machine according to methods that are well known in the art. In various embodiments of the invention, the milled mexiletine hydrochloride granules can be blended with microcrystalline cellulose, a glidant, such as, for example, silicon dioxide, in some embodiments colloidal silica, and a lubricant, such, for example, magnesium stearate.

In various embodiments of the invention, the mexiletine hydrochloride blend can be compressed into pellets using tooling according to methods known in the art. For example, in various embodiments of the invention, the blend of granulated mexiletine can be compressed into tablets or pellets. In various embodiments of the invention, the mexiletine pellets can be coated with a polyvinyl alcohol (PVA)-based polymeric film coating by any suitable technique, of which several are known in the art. In various embodiments, the polymeric film coating can comprise an Opadry film coating available from Colorcon, Inc. (Harleysville, PA). In various embodiments, the coating can be performed with a pan coater or a fluidized bed coater according to methods known in the art.

In various embodiments of the invention, a dofetilide component can be prepared by dry blending dofetilide with various excipients. In various embodiments of the invention, micronized dofetilide is geometrically mixed with pregelatinized starch, microcrystalline cellulose, silicon dioxide (in some embodiments colloidal silica), and magnesium stearate. In various embodiments, the dofetilide blend can be further compressed into tablets using tooling according to previously established methods. In various embodiments, the dofetilide blend can be compressed into tablets or pellets.

In various embodiments of the invention, dofetilide tablets can be coated with polyvinyl alcohol (PVA) by any known technique. In some embodiments, the coating is performed with a pan coater or a fluidized bed coater according to methods known in the art. In a further embodiment of the invention, a hard capsule is filled with coated dofetilide tablets or pellets and coated mexiletine hydrochloride tablets or pellets. In various embodiments of the invention, the dofetilide tablets or pellets and mexiletine tablets or pellets can be filled into a hard capsule.

Various other embodiments of the invention include methods of treating atrial fibrillation or a symptom associated therewith in a subject in need thereof comprising administering to the subject 100 mcg to 1000 mcg dofetilide, or higher (up to, for example, 1500 mcg), and 100 mg to 1000 mg mexiletine hydrochloride, in some embodiments in a capsule according to any of the preceding formulation embodiments. For example, the method can comprise administering to a subject in need thereof a pharmaceutical composition, such as a capsule, comprising 100-500 mcg, 505-600 mcg, 605-700 mcg, 705-800 mcg, 805-900 mcg, or 905-1000 mcg dofetilide, and 100 mg mexiletine HCl, 200 mg mexiletine HCl, 300 mg mexiletine HCl, 400 mg mexiletine HCl, 500 mg mexiletine HCl, 600 mg mexiletine HCl, 700 mg mexiletine HCl, 800 mg mexiletine HCl, 900 mg mexiletine HCl, or 1000 mg mexiletine HCl, and a pharmaceutically acceptable carrier. The method can also comprise administering to a subject in need thereof a first pharmaceutical composition, such as a capsule, comprising 100 mg, 200 mg, 300 mg, 400 mg or 500 mg mexiletine HCl, and a pharmaceutically acceptable carrier, and a second pharmaceutical composition, such as a capsule, comprising 100-500 mcg, 505-600 mcg, 605-700 mcg, 705-800 mcg, 805-900 mcg, or 905-1000 mcg dofetilide, and a pharmaceutically acceptable carrier.

EXAMPLES

The invention will now be described in further detail with reference to the following specific, non-limiting examples. However, those of skill in the art should, in light of the present disclosure, appreciate that many changes can be made in the specific embodiments which are disclosed and still obtain a like or similar result without departing from the scope of the invention.

Example 1

Mexiletine hydrochloride was granulated with Avicel PH101 using an aqueous binder solution of Povidone K29/32. The granules were dried in the oven at 55° C. and milled using a FitzMill comminuting device. The milled mexiletine HCl granules were blended with Avicel PH102, Cab-O-Sil, and magnesium stearate. The mexiletine HCl blend was compressed into 7 mg pellets using 2.0 mm tooling. The mexiletine HCl core pellets were coated with polyvinyl alcohol (PVA) based-Opadry. The formulation for the mexiletine HCl Pellets is provided in Table 1 below. A dofetilide blend was made by geometrically mixing micronized dofetilide with starch 1500, Avicel PH101, Cab-O-Sil, and magnesium stearate. The dofetilide blend was compressed into 85 mg tablets using 5.6 mm tooling. The formulation for dofetilide tablets is presented in Table 2. Pharmaceutical compositions in unit dosage form in accordance with this Example were manufactured by filling Size 0EL hard gelatin capsule with one dofetilide tablet and coated mexiletine HCl pellets at dofetilide and mexiletine HCl strengths of 500 mcg and 275 mg, respectively. These capsules presented an immediate-release drug profile.

TABLE 1

| Mexiletine HCl Pellets 71.4%—Formulation | | |
|---|---|---|
| Ingredients | mg/gram | % w/w |
| Mexiletine HCl USP | 714.29 | 71.43 |
| Microcrystalline Cellulose, NF (Avicel PH101) | 77.40 | 7.74 |
| Povidone, USP (Plasdone K29/32) | 18.18 | 1.82 |
| Purified Water, USP$^{(1)}$ | N/A | N/A |
| Microcrystalline Cellulose, NF (Avicel PH102) | 90.91 | 9.09 |
| Colloidal Silicon Dioxide (Cab-O-Sil ®), NF | 4.155 | 0.42 |
| Magnesium Stearate, NF [Vegetable Source] | 4.155 | 0.42 |
| Theoretical Total Weight—Pellets Core | 909.09 | 90.91 |
| Opadry II 85F140062 Pink | 90.91 | 9.09 |
| Purified Water, USP$^{(1)}$ | N/A | N/A |
| Theoretical Total Weight—Coated Pellets | 1000.0 | 100.0 |

Note:
$^{(1)}$Purified Water, USP is used in manufacturing but does not appear in the final product.

TABLE 2

| Dofetilide Tablets, 0.59%—Formulation | | |
|---|---|---|
| Ingredients | mg/gram | % w/w |
| Dofetilide, USP (Micronized) | 5.88 | 0.59 |
| Pregelatinized Starch, NF (Starch 1500) | 500.00 | 50.00 |
| Microcrystalline Cellulose, NF (Avicel PH 101) | 490.12 | 49.01 |
| Colloidal Silicon Dioxide (Cab-O-Sil ®), NF | 2.00 | 0.2 |
| Magnesium Stearate, NF [Vegetable Source] | 2.00 | 0.2 |
| Theoretical Total Weight—Pellets Core | 1000.00 | 100.0 |

The capsules were tested for stability at room temperature and accelerated condition of 40° C./75% relative humidity ("RH") and the data are shown in Table 3.

TABLE 3

| | Stability of Example 1 Capsules, 500 mcg/275 mg | | | | | |
|---|---|---|---|---|---|---|
| | | | Time Point | | | |
| | T0 | 1 Month | | 2 Months | 3 Months | |
| | | | Condition | | | |
| | Room Temp. | Room Temp. | 40° C./75% RH | 40° C./75% RH | Room Temp. | 40° C./75% RH |
| | | | Dofetilide | | | |
| Assay (%) | 98.67 | 100.49 | 98.21 | 96.78 | 98.25 | 96.76 |
| | | | Impurities | | | |
| RRT 0.88 | <QL | <QL | 0.10 | 0.1 | <QL | 0.18 |
| RRT 1.23 | <QL | <QL | 0.27 | 0.54 | 0.14 | 0.79 |
| Total | 0.0 | 0.0 | 0.37 | 0.64 | 0.14 | 0.97 |

TABLE 3-continued

Stability of Example 1 Capsules, 500 mcg/275 mg

| | Time Point | | | | | |
|---|---|---|---|---|---|---|
| | T0 | 1 Month | | 2 Months | 3 Months | |
| | | | Condition | | | |
| | Room Temp. | Room Temp. | 40° C./75% RH | 40° C./75% RH | Room Temp. | 40° C./75% RH |
| Mexiletine | | | | | | |
| Assay | 98.99 | 98.95 | 97.58 | 98.79 | 98.05 | 98.64 |
| Impurities | | | | | | |
| 2,6-DMP | ND | ND | ND | ND | ND | ND |
| MX-200 | <QL | <QL | <QL | <QL | <QL | < QL |
| MX-300 | <QL | <QL | <QL | <QL | <QL | < QL |
| Total | 0.0 | 0.0 | 0.0 | 0.0 | 0.0 | 0.0 |

Note:
Percentages given in reference to compositions throughout the specification are percentages by weight (w/w) unless indicated otherwise. The term "QL" stands for quantitation limit, the lowest concentration which can be not only detected, but also quantified with a specified degree of precision.

Example 2

Mexiletine HCl was granulated with Avicel PH101 using aqueous binder solution of Povidone K29/32. The granules were dried in the oven at 55° C. and milled using a FitzMill.

The milled mexiletine HCl granules were blended with Avicel PHT02, Cab-O-Sil, and magnesium stearate. The mexiletine HCl blend was compressed into 7 mg pellets using 2.0 mm tooling. The mexiletine HCl core pellets were coated with polyvinyl alcohol (PVA) based-Opadry. The formulation for mexiletine HCl Pellets is provided in Table 4. A dofetilide blend was made by geometrically mixing the micronized dofetilide with starch 1500, Avicel PH101, Cab-O-Sil, and magnesium stearate. The dofetilide blend was compressed into 85 mg tablets using 5.6 mm tooling. The dofetilide core tablets were coated with polyvinyl alcohol (PVA) based-Opadry. The formulation for dofetilide tablets is presented in Table 5. Pharmaceutical compositions in unit dosage form in accordance with this Example were manufactured by filling Size OEL hard gelatin capsule with one coated dofetilide tablet and coated mexiletine HCl pellets at dofetilide and mexiletine HCl strengths of 500 mcg and 275 mg, respectively.

TABLE 4

Mexiletine HCl Pellets 71.4%—Formulation

| Ingredients | mg/gram | % w/w |
|---|---|---|
| Mexiletine HCl USP | 714.29 | 71.43 |
| Microcrystalline Cellulose, NF (Avicel PH101) | 77.40 | 7.74 |
| Povidone, USP (Plasdone K29/32) | 18.18 | 1.82 |
| Purified Water, USP[(1)] | N/A | N/A |
| Microcrystalline Cellulose, NF (Avicel PH102) | 90.91 | 9.09 |
| Colloidal Silicon Dioxide (Cab-O-Sil ®), NF | 4.155 | 0.42 |
| Magnesium Stearate, NF [Vegetable Source] | 4.155 | 0.42 |
| Theoretical Total Weight—Pellets Core | 909.09 | 90.91 |

TABLE 4-continued

Mexiletine HCl Pellets 71.4%—Formulation

| Ingredients | mg/gram | % w/w |
|---|---|---|
| Opadry II 85F140062 Pink | 90.91 | 9.09 |
| Purified Water, USP[(1)] | N/A | N/A |
| Theoretical Total Weight—Coated Pellets | 1000.0 | 100.0 |

Note:
[(1)]Purified Water, USP is used in manufacturing but does not appear in the final product.

TABLE 5

Dofetilide Tablets, 0.53%—Formulation

| Ingredients | mg/gram | % w/w |
|---|---|---|
| Dofetilide, USP (Micronized) | 5.348 | 0.53 |
| Pregelatinized Starch, NF (Starch 1500) | 454.55 | 45.46 |
| Microcrystalline Cellulose, NF (Avicel PH 101) | 445.56 | 44.56 |
| Colloidal Silicon Dioxide (Cab-O-Sil ®), NF | 1.816 | 0.18 |
| Magnesium Stearate, NF [Vegetable Source] | 1.816 | 0.18 |
| Theoretical Total Weight—Pellets Core | 909.09 | 90.91 |
| Opadry II 85F90892 Blue | 90.91 | 9.09 |
| Purified Water, USP[(1)] | N/A | N/A |
| Theoretical Total Weight—Coated Pellets | 1000.0 | 100.00 |

Note:
[(1)]Purified Water, USP is used in manufacturing but does not appear in the final product.

The capsules of this Example exhibited immediate release characteristics for dofetilide and mexiletine initially and after one-month storage at accelerated stability condition of 40° C./75% RH.

The capsules were tested for stability at room temperature and accelerated condition of 40° C./75% RH and the testing data are shown in Table 6.

TABLE 6

Stability of Example 2 Capsules, 500 mcg/275 mg

| | | | Time Point | | | |
|---|---|---|---|---|---|---|
| | T0 | 1 month | | 2 months | 3 months | |
| | | | Condition | | | |
| | Room Temp. | Room Temp. | 40° C./75% RH | 40° C./75% RH | Room Temp. | 40° C./75% RH |
| Dofetilide | | | | | | |
| Assay (%) | 99.21 | 99.82 | 98.78 | 99.46 | 100.27 | 99.11 |
| Impurities | | | | | | |
| RRT 0.88 | <QL | <QL | <QL | 0.10 | <QL | 0.15 |
| RRT 1.23 | <QL | <QL | 0.16 | 0.32 | 0.14 | 0.48 |
| Total | 0.0 | 0.0 | 0.16 | 0.42 | 0.14 | 0.63 |
| Mexiletine | | | | | | |
| Assay | 98.42 | 99.16 | 97.85 | 97.93 | 99.69 | 97.87 |
| Impurities | | | | | | |
| 2,6-DMP | ND | ND | ND | ND | ND | ND |
| MX-200 | <QL | <QL | <QL | <QL | <QL | <QL |
| MX-300 | <QL | <QL | <QL | <QL | <QL | <QL |
| Total | 0.0 | 0.0 | 0.0 | 0.0 | 0.0 | 0.0 |

Reference to unknown impurities is made by providing relative retention times ("RRT"). Reference to identified impurities is made by referring expressly to them, such as referring to 2,6-DMP (2,6-dimethylphenol), MX-200 (3,9-dimethyl-2,3-dihydro-1,4-benzoxazepine), and MX-300 (2-hydroxy-3-methylbenzaldehyde).

Comparative Example 1

Dry Blending of Dofetilide with Mexiletine Granules

Dry blend filled capsules (Table C3) of Comparative Example 1 were manufactured by granulating mexiletine hydrochloride with an aqueous binder solution of 0.5 mg of Hypromellose, HPMC E5 LV and 31 mg of purified water as a solvent. The granules were then dried in the oven at 55° C. and milled with a Fitzmill comminuting machine. Micronized dofetilide was geometrically mixed with 48 mg of pregelatinized starch (Starch 1500) and 98 mg of microcrystalline cellulose (Avicel PH 101). The mexiletine granulation and dofetilide blend were mixed with 2.2 mg of Cab-O-Sil® at dofetilide and mexiletine HCl strengths of 250 mcg and 275 mg, respectively. The blend was further lubricated with 1.0 mg of magnesium stearate. The resulting blend was then filled in size 0 hard gelatin capsules.

The capsules of Comparative Example 1 exhibited immediate release characteristics for dofetilide and mexiletine hydrochloride. Importantly, micronized dofetilide and the optimized geometric mixing process resulted in good content uniformity of both mexiletine hydrochloride and dofetilide drug substances (Table C4).

TABLE C3

Formulation of Mexiletine Granulation and Dry Blended Dofetilide

| Ingredients | mg/unit | % w/w |
|---|---|---|
| Part I: Granulation of Mexiletine | | |
| Mexiletine HCl, USP | 275.0 | 64.7 |
| Hypromellose (HPMC E5 LV) | 0.5 | 0.1 |

TABLE C3-continued

Formulation of Mexiletine Granulation and Dry Blended Dofetilide

| Ingredients | mg/unit | % w/w |
|---|---|---|
| Purified Water* | 31.0 | — |
| Part II: Geometric mixing of Dofetilide | | |
| Dofetilide USP, Micronized | 0.25 | 0.06 |
| Pregelatinized Starch (Starch 1500) | 48.0 | 11.3 |
| Microcrystalline Cellulose (Avicel PH 101) | 98.0 | 23.1 |
| Part III | | |
| Colloidal Silicon Dioxide (Cab-O-Sil ®) | 2.2 | 0.5 |
| Magnesium stearate | 1.0 | 0.2 |
| Total Fill Weight | 425.0 | 100.0 |

*The solvent is evaporated during the process and will not appear in the final product

TABLE C4

Content Uniformity of Comparative Example 1

| Attribute | Dofetilide (%) | Mexiletine (%) | Fill Weight (mg) |
|---|---|---|---|
| Average | 100.1 | 92.6 | 423.7 |
| RSD (%) | 5.5 | 1.3 | 1.9 |
| Range | 89.4-108.6 | 90.4-94.0 | 480.7-436.3 |
| Acceptance Value | 13.4 | 8.8 | N/A |

Impurity analysis in the context of this invention was performed according to standard high performance liquid chromatography (HPLC) with detection by ultra-violet spectroscopy (UV), finding one or more of the impurity's mass, relative retention time, and amount (as relative area percentage), and they are provided herein by using notation that is typical in such standard methodologies. For an illustrative review of the same see, for example, S. Levin, "High Performance Liquid Chromatography (HPLC) in the pharmaceutical analysis", Medtechnica (2010), which is incorporated herein by reference (describing HPLC modes, HPLC theory, the role of HPLC in drug analysis, and specialized HPLC separations). The initial stability of the batch showed almost no impurities detected. However, after 1-month storage at accelerated stability condition (40° C./75% RH), the dofetilide related impurities increased significantly. In particular, an oxidative degradation product of dofetilide (dofetilide related impurity 6) formed. It is possible that the interaction of mexiletine hydrochloride and dofetilide resulted in higher impurities of dofetilide. Given that mexiletine hydrochloride is a basic compound and present at a relatively higher level (1100 times that of dofetilide), mexiletine hydrochloride could affect the stability of dofetilide.

In summary, Comparative Example 1 exhibited immediate release characteristics for dofetilide and mexiletine hydrochloride as well as good content uniformity, but the stability was lower than that shown in the preceding examples due to impurities that increased over time.

TABLE C5

Stability of Comparative Example 1 (0.25 mg/275 mg)

| Impurity | RRT (min) | Impurities (% w/w) | | |
|---|---|---|---|---|
| | | Initial | 1 Month 40° C./ 75% RH | 1 Month Room Temp. |
| Mexiletine Related Compound A | 0.44 | 0 | 0 | 0 |
| Mexiletine unknown impurity 1 | 1.06 | 0 | 0 | 0 |
| Mexiletine unknown impurity 2 | 1.36 | 0.01 | 0 | 0 |
| Total Mexiletine related impurities | — | 0.01 | 0 | 0 |
| Dofetilide Related Compound A | 0.54 | 0 | 0.14 | 0 |
| Dofetilide unknown impurity 1 | 0.79 | 0 | 0.16 | 0 |
| Dofetilide unknown impurity 2 | 0.8 | 0 | 0.05 | 0 |
| Dofetilide unknown impurity 3 | 0.81 | 0 | 0.36 | 0 |
| Dofetilide unknown impurity 4 | 0.84 | 0 | 0.19 | 0 |
| Dofetilide unknown impurity 5 | 0.88 | 0 | 0 | 0.8 |
| Dofetilide unknown impurity 6 | 1.21 | 0 | 1.33 | 0 |
| Total Dofetilide related impurities | — | 0.00 | 2.23 | 0.80 |

Example 3

A study was performed to examine the relative bioavailability of the test product dofetilide and mexiletine from FBHRS001®, Dofetilide/Mexiletine HCl Capsules, 500 mcg/275 mg, versus the reference products Tikosyn® (dofetilide) Capsules 500 mcg (0.5 mg) and Mexiletine Hydrochloride Capsules USP, 250 mg given once concomitantly to healthy male and non-pregnant female volunteers under fasting conditions. The difference between the 275 mg of mexiletine HCl in the test product Dofetilide/Mexiletine HCl Capsules, and 250 mg of mexiletine HCl in one of the reference products, is regarded as acceptable in the context of this study. This consideration also applies to similar differences in amounts of the same API in additional examples provided herein. Potential subjects were subject to selection criteria based on a plurality of factors such as age, healthy habits, BMI, cardiovascular conditions, diet, behavioral incompatibilities, availability to pursue the entire study, pregnancy and contraception measures for women and men, blood chemistry, known history or presence of certain clinically significant conditions and abnormalities, positive test to certain conditions or to ingestion/administration/use of specified agents, deficiencies, allergies and intolerances, and participation in other trials.

Test and reference products were administered to subjects in study periods under certain time and diet conditions. Samples from 18 subjects were analyzed by the bioanalytical laboratory. Data from 18 subjects were included in the pharmacokinetic and statistical analysis. The concentration of dofetilide and mexiletine were measured from plasma samples collected over a 48-hour interval after dosing in each period. Pharmacokinetic parameters $C_{max}$, $T_{max}$, $AUC_t$, $AUC_{inf}$, T½ and λ were estimated based on dofetilide and mexiletine plasma levels for subjects included in the statistical analysis.

Results

The test product FBHRS001®, Dofetilide/Mexiletine HCl Capsules, 500 mcg/275 mg demonstrated a comparable rate and extent of absorption of dofetilide to the reference product Tikosyn® (dofetilide) capsules 500 mcg (0.5 mg). The test/reference (T/R) geometric mean ratios (GMR) were approximately 100% for $AUC_t$ (area under plasma concentration time-curve from time zero) and at 0.5, 1, 1.5, 2, 2.5, 3, 4, 6, 9, 12, 16, 24, 36 and 48 hours post-dose in each study period. $AUC_{inf}$ (area under plasma concentration-time curve from time 0 to infinity) and $C_{max}$ (maximum observed plasma concentration) and the corresponding 90% CIs (confidence intervals) for $AUC_t$, $AUC_{inf}$ and $C_{max}$ were contained within the FDA-acceptance range 80.00%-125.00%.

The test product FBHRS001®, Dofetilide/Mexiletine HCl Capsules, 500 mcg/275 mg demonstrated a comparable rate and extent of absorption of mexiletine. The reference product Mexiletine Hydrochloride Capsules USP, 250 mg exhibited test/reference (T/R) geometric mean ratios (GMR) of approximately 108% for $AUC_t$ and $AUC_{inf}$ and 110% for $C_{max}$ with the corresponding 90% CIs for $AUC_t$, $AUC_{inf}$ and $C_{max}$ contained within the FDA-acceptance range 80.00%-125.00%.

Therefore, comparative bioavailability was demonstrated between the test product FBHRS001®, Dofetilide/Mexiletine HCl Capsules, 500 mcg/275 mg and the reference product Tikosyn® (dofetilide) Capsules 500 mcg (0.5 mg), and Mexiletine Hydrochloride Capsules USP, 250 mg in healthy non-smoking male and non-pregnant female volunteers under fasting conditions. Consequently, administration of FBHRS001®, Dofetilide/Mexiletine HCl Capsules, 500 mcg/275 mg is equivalent to co-administration of commercially available dofetilide and mexiletine as separate entities Example 4

A study was performed to examine the relative bioavailability of dofetilide and mexiletine from FBHRS001® Dofetilide/Mexiletine HCl Capsules, 500 mcg/245 mg versus TIKOSYN®, (dofetilide) Capsules, and 500 mcg and Mexiletine Hydrochloride Capsules USP 250 mg given separately in each period to healthy male and non-pregnant female volunteers under fasting conditions. Another objective of the study was to evaluate the effect of food (high-fat meal vs fasting) in the bioavailability of the fixed-dosed combination FBHRS001® Dofetilide/Mexiletine HCl Capsules, 500 mcg/245 mg to healthy male and non-pregnant female volunteers. Potential subjects were subject to selection criteria based on a plurality of factors such as those summarized in Example 3. Test and reference products were administered to subjects in study periods under specified time and diet conditions. Data from twenty-six (26) subjects were included in the pharmacokinetic and statistical analyses and comparisons under different conditions.

Results

The test product A (FBHRS001® Dofetilide/Mexiletine HCl Capsules, 500 mcg/245 mg) demonstrated a comparable rate and extent of absorption of dofetilide to the reference product B (TIKOSYN®, (dofetilide) Capsules, 500 mcg). Descriptive statistics (min, max, median, mean, standard deviation and coefficient of variation) of all pharmacokinetic parameters were provided for dofetilide and mexiletine for the Test and Reference products.

Parameters for $AUC_t$, $AUC_{inf}$ and $C_{max}$ were transformed prior to analysis using a natural logarithmic transformation. ANOVA was performed on the un-transformed data for T½, k, $T_{max}$, Tlag (if applicable) and on the ln-transformed data for $AUC_t$, $AUC_{inf}$ and $C_{max}$, Tmax and Tlag (if applicable) were analyzed using an additional non-parametric test (Wilcoxon test). 90% confidence intervals (CI) ratios of geometric means for $AUC_t$, AUCinf and Cmax were calculated based on the LSMEANS and ESTIMATE of the ANOVA. For an absence of food effect on Dofetilide and mexiletine bioavailability, the 90% confidence interval for the ratios of the geometric means between fed and fasting treatments, based on ln-transformed data, should be contained within 80%-125% for $AUC_t$, $AUC_{inf}$ and $C_{max}$. The test/reference A/B geometric mean ratios (GMR) were approximately 98%, 98%, and 96% for $AUC_t$, $AUC_{inf}$ and $C_{max}$, respectively and the corresponding 90% CIs for $AUC_t$ were contained within the FDA-acceptance range of 80%-125%. The test product A (FBHRS001® Dofetilide/Mexiletine HCl Capsules, 500 mcg/245 mg) demonstrated a comparable rate and extent of absorption of mexiletine to the reference product C (Mexiletine Hydrochloride Capsules USP 250 mg). The test/reference (A/C) geometric mean ratios (GMR) were approximately 97%, 97%, and 97% for $AUC_t$, $AUC_{inf}$ and $C_{mx}$, respectively and the corresponding 90% CIs for $AUC_t$ were contained within the FDA-acceptance range 80.00%-125.00%. Hence, comparative bioavailability was demonstrated between test product A (FBHRS001® Dofetilide/Mexiletine HCl Capsules, 500 mcg/245 mg), reference product B (TIKOSYN®, (dofetilide) Capsules, 500 mcg), and reference product C (Mexiletine Hydrochloride Capsules USP 250 mg) in healthy, non-smoking, male and non-pregnant female volunteers under fasting conditions. The test product FBHRS001® Dofetilide/Mexiletine HCl Capsules, 500 mcg/245 mg demonstrated a comparable rate and extent of absorption of dofetilide under fed (Product D) and fasting conditions (Product A). The test product D/test product A (fed/fasting) geometric mean ratios (GMR) were approximately 102%, 101%, and 114% for $AUC_t$, $AUC_{inf}$ and $Cm_x$, respectively and the corresponding 90% CIs were contained within the FDA-acceptance range 80.00%-125.00%. The test product FBHRS001® Dofetilide/ Mexiletine HCl Capsules, 500 mcg/245 mg demonstrated a comparable rate and extent of absorption of mexiletine under fed (Product D) and fasting conditions (Product A). The test product D/test product A (fed/fasting) geometric mean ratios (GMR) were approximately 97%, 97%, and 92% for $AUC_t$, $AUC_{inf}$ and $C_{max}$, respectively. The corresponding 90% CIs were contained within the FDA-acceptance range 80.00%-125.00%. Consequently, there was an absence of a food effect on the bioaviliaility of dofetilide/ mexiletine for FBHRS001® Dofetilide/Mexiletine HCl Capsules, 500 mcg/245 mg in healthy, non-smoking male and non-pregnant female volunteers. Additionally, there was no drug-drug interaction of the APIs observed for FBHRS001® Dofetilide/Mexiletine HCl Capsules, 500 mcg/245 mg.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

REFERENCES

1. Guo Y, Tian Y, Wang H, Si Q, Wang Y, Lip G Y. Prevalence, incidence, and lifetime risk of atrial fibrillation in China: new insights into the global burden of atrial fibrillation. Chest 2015; 147: 109-119.
2. Chei C L, Raman P, Ching C K, Yin Z X, Shi X M, Zeng Y, Matchar D B. Prevalence and Risk Factors of Atrial Fibrillation in Chinese Elderly: Results from the Chinese Longitudinal Healthy Longevity Survey. Chin Med J (Engl) 2015; 128: 2426-2432.
3. Chugh S S, Havmoeller R, Narayanan K, Singh D, Rienstra M, Benjamin E J, Gillum R F, Kim Y H, McAnulty J H, Jr., Zheng Z J, Forouzanfar M H, Naghavi M, Mensah G A, Ezzati M, Murray C J. Worldwide epidemiology of atrial fibrillation: a Global Burden of Disease 2010 Study. Circulation 2014; 129: 837-847.
4. Colilla S, Crow A, Petkun W, Singer D E, Simon T, Liu X. Estimates of current and future incidence and prevalence of atrial fibrillation in the U.S. adult population. Am J Cardiol 2013; 112: 1142-1147.
5. Suttorp M J, Polak P E, van 't H A, Rasmussen H S, Dunselman P H, Kingma J H. Efficacy and safety of a new selective class III antiarrhythmic agent Dofetilide in paroxysmal atrial fibrillation or atrial flutter. Am J Cardiol 1992; 69: 417-419.
6. Rasmussen H S, Allen M J, Blackburn K J, Butrous G S, Dalrymple H W. Dofetilide, a novel class III antiarrhythmic agent. J Cardiovasc Pharmacol 1992; 20 Suppl 2: 596-105.
7. Zimetbaum P. Antiarrhythmic drug therapy for atrial fibrillation. Circulation 2012; 125: 381-389.
8. Qin D, Leef G, Alam M B, Rattan R, Munir M B, Patel D, Khattak F, Adelstein E, Jain S K, Saba S. Comparative effectiveness of antiarrhythmic drugs for rhythm control of atrial fibrillation. J Cardiol 2015.
9. Aktas M K, Shah A H, Akiyama T. Dofetilide-induced long QT and torsades de pointes. Ann Noninvasive Electrocardiol 2007; 12: 197-202.
10. Qi D, Yang Z, Robinson V M, Li J, Gao C, Guo D, Kowey P R, Yan G X. Heterogeneous distribution of INa-L determines interregional differences in rate adaptation of repolarization. Heart Rhythm 2015; 12: 1295-1303.
11. Badri M, Patel A, Patel C, Liu G, Goldstein M, Robinson V M, Li J, Xue X, Yang L, Kowey P R, Yan G X. Mexiletine Prevents Recurrent Torsades de Pointes in Acquired Long QT Syndrome Refractory to Conventional Measures. JACC: Clinical Electrophysiology 2015; 1: 315-322.
12. Yan G X, Wu Y, Liu T, Wang J, Marinchak R A, Kowey P R. Phase 2 early afterdepolarization as a trigger of polymorphic ventricular tachycardia in acquired long-QT syndrome: direct evidence from intracellular recordings in the intact left ventricular wall. Circulation 2001; 103: 2851-2856.
13. Talbot R G, Nimmo J, Julian D G, Clark R A, Neilson J M, Prescott L F. Treatment of ventricular arrhythmias with mexiletine (Ko 1173). Lancet 1973; 2: 399-404.
14. Campbell N P, Kelly J G, Shanks R G, Chaturvedi N C, Strong J E, Pantridge J F. Mexiletine (Ko 1173) in the management of ventricular dysrhythmias. Lancet 1973; 2: 404-407.
15. Miller J M, Zipes D P. Therapy for Cardiac Arrhythmias. In: Mann D. L., Zipes D. P., Libby P., Bonow J. O. (eds) Braunwald's Heart Disease: A Textbook of Cardiovascular Medicine. Elsevier Publisher. 2014: 693.
16. January C T, Wann L S, Alpert J S, Calkins H, Cigarroa J E, Cleveland J C, Jr., Conti J B, Ellinor P T, Ezekowitz M D, Field M E, Murray K T, Sacco R L, Stevenson W G, Tchou P J, Tracy C M, Yancy C W. 2014 AHA/ACC/HRS guideline for the management of patients with atrial fibrillation: executive summary: a report of the American College of Cardiology/American Heart Association Task Force on practice guidelines and the Heart Rhythm Society. Circulation 2014; 130: 2071-2104.

What is claimed is:

1. A pharmaceutical composition in unit dosage form comprising:
a) a dofetilide component; and
b) a mexiletine component;
wherein said dofetilide component and said mexiletine component are contained within a single dosage form;
wherein at least one of the two components chosen from said dofetilide component and said mexiletine component is coated with a coating, and said unit dosage form has an immediate-release profile for said dofetilide component and for said mexiletine component;
wherein said unit dosage form contains one of the following (a), (b) or (c) compositions: (a) about 500 mcg dofetilide and about 275 mg mexiletine hydrochloride, (b) about 500 mcg dofetilide and about 245 mg mexiletine hydrochloride, (c) about 250 mcg dofetilide and about 245 mg mexiletine hydrochloride;
wherein said unit dosage form is a capsule,
wherein said mexiletine component comprises a plurality of pellets, each of said pellets having a pellet core that is uncoated or coated with a pellet coating,
wherein each of said pellet cores comprises a mixture of mexiletine hydrochloride and pellet excipients,
wherein each of said pellet cores contains from about 70% to about 80% by weight of mexiletine hydrochloride and each of said pellet cores contains about 2% by weight of povidone, and wherein said dofetilide component comprises a tablet, said tablet comprises a mixture of dofetilide and tablet excipients, said tablet is uncoated or coated with a tablet coating, and said coated or uncoated tablet contains from about 0.5% to about 0.6% by weight of dofetilide;
wherein said mixture of mexiletine hydrochloride and pellet excipients is a mixture of (i) a blend of mexiletine hydrochloride, a polyvinylpyrrolidone binder, and a first microcrystalline cellulose, with (ii) a second microcrystalline cellulose, colloidal silica and magnesium stearate,
wherein said pellet coating, when said pellet is coated, is a polyvinyl alcohol polymeric film coating, and said pellet coating is present in an amount of about 9.1% by weight of said coated pellet,
wherein said pellet core contains an amount of about 10% by weight of said second microcrystalline cellulose, and said first microcrystalline cellulose and said second microcrystalline cellulose in each of said pellet cores have different particle sizes, and
wherein said tablet coating, when said tablet is coated, is a polyvinyl alcohol polymeric film coating, and said tablet coating is present in an amount of about 9.1% by weight of said coated tablet.

2. The pharmaceutical composition of claim 1, wherein said at least one of the two components chosen from said dofetilide component and said mexiletine component is compressed.

3. The pharmaceutical composition of claim 1, wherein said tablet excipients comprise colloidal silica and magnesium stearate.

4. The pharmaceutical composition in unit dosage form of claim 1,
wherein said dofetilide component has impurities analyzed over time that satisfy at least one of the three characteristics chosen from the following (a), (b) and (c):
(a) below quantitation limit at room temperature and less than 0.5% under 40° C./75% RH conditions one month after the pharmaceutical composition in unit dosage form was prepared,
(b) less than 0.8% under 40° C./75% RH conditions two months after the pharmaceutical composition in unit dosage form was prepared, and
(c) less than 0.3% at room temperature and less than 1% under 40°° C./75% RH conditions three months after the pharmaceutical composition in unit dosage form; and
wherein said mexiletine component has impurities analyzed over time that satisfy at least one of the three characteristics chosen from the following (d), (e) and (f):
(d) below quantitation limit at room temperature and under 40° C./75% RH conditions one month after the pharmaceutical composition in unit dosage form was prepared,
(e) below quantitation limit under 40° C./75% RH conditions two months after the pharmaceutical composition in unit dosage form was prepared, and
(f) below quantitation limit at room temperature and under 40° C./75% RH conditions three months after the pharmaceutical composition in unit dosage form was prepared.

5. The pharmaceutical composition in unit dosage form of claim 4,
wherein said dofetilide component has impurities analyzed over time that satisfy at least one of the three characteristics chosen from the following (a), (b) and (c):
(a) below quantitation limit at room temperature and less than 0.2% under 40° C./75% RH conditions one month after the pharmaceutical composition in unit dosage form was prepared,
(b) less than 0.5% under 40°° C./75% RH conditions two months after the pharmaceutical composition in unit dosage form was prepared, and
(c) less than 0.2% at room temperature and less than 0.7% under 40° C./75% RH conditions three months after the pharmaceutical composition in unit dosage form was prepared; and
wherein said mexiletine component has impurities analyzed over time that satisfy at least one of the three characteristics chosen from the following (d), (e) and (f):

(d) below quantitation limit at room temperature and under 40° C./75% RH conditions one month after the pharmaceutical composition in unit dosage form was prepared,
(e) below quantitation limit under 40° C./75% RH conditions two months after the pharmaceutical composition in unit dosage form was prepared, and
(f) below quantitation limit at room temperature and under 40° C./75% RH conditions three months after the pharmaceutical composition in unit dosage form was prepared.

6. A method of treating or preventing atrial fibrillation or a symptom associated therewith in a subject in need thereof, the method comprising administering to the subject the pharmaceutical composition of claim 4.

7. A method of preparing the pharmaceutical composition of claim 4, comprising: obtaining the dofetilide component and the mexiletine component, and placing the dofetilide component and the mexiletine component within a capsule.

8. The method according to claim 7, wherein said placing said dofetilide component and said mexiletine component within said capsule comprises filling a gelatin capsule with at least one coated dofetilide tablet and at least one uncoated mexiletine pellet.

9. The method according to claim 7, wherein said placing the dofetilide component and the mexiletine component within the capsule comprises filling a gelatin capsule with at least one uncoated dofetilide tablet and at least one coated mexiletine pellet.

10. The method according to claim 8, wherein manufacturing said coated dofetilide tablet comprises
    geometrically mixing micronized dofetilide with starch, microcrystalline cellulose, colloidal silicon dioxide and magnesium stearate, yielding a dofetilide blend;
    compressing said dofetilide blend, yielding a dofetilide tablet; and
    coating said dofetilide tablet with polyvinyl alcohol polymeric film coating yielding a coated dofetilide tablet.

11. The method according to claim 9, wherein manufacturing said uncoated dofetilide tablet comprises
    geometrically mixing micronized dofetilide with starch, microcrystalline cellulose, colloidal silicon dioxide and magnesium stearate, yielding a dofetilide blend; and
    compressing said dofetilide blend, yielding an uncoated dofetilide tablet.

12. The method according to claim 8, wherein manufacturing said uncoated mexiletine pellet comprises
    granulating mexiletine hydrochloride with the first microcrystalline cellulose and with the polyvinylpyrrolidone binder yielding a mexiletine granule;
    drying said mexiletine granule yielding a dry mexiletine granule;
    milling said dry mexiletine granule yielding a milled mexiletine granule;
    blending said milled mexiletine granule with the second microcrystalline cellulose, colloidal silicon dioxide and magnesium stearate yielding a mexiletine blend; and
    compressing said mexiletine blend yielding an uncoated mexiletine pellet.

13. The method according to claim 9, wherein manufacturing said coated mexiletine pellet comprises
    granulating mexiletine hydrochloride with the first microcrystalline cellulose and with the polyvinylpyrrolidone binder yielding a mexiletine granule;
    drying said mexiletine granule yielding a dry mexiletine granule;
    milling said dry mexiletine granule yielding a milled mexiletine granule;
    blending said milled mexiletine granule with the second microcrystalline cellulose, colloidal silicon dioxide and magnesium stearate yielding a mexiletine blend;
    compressing said mexiletine blend yielding a mexiletine pellet; and
    coating said mexiletine pellet with polyvinyl alcohol polymeric film coating yielding a coated mexiletine pellet.

14. The method of preparing the pharmaceutical composition of claim 4, comprising: obtaining the dofetilide component and the mexiletine component, and placing the dofetilide component and the mexiletine component within a capsule,
    wherein said placing said dofetilide component and said mexiletine component within said capsule comprises
    (a) filling a gelatin capsule with at least one coated dofetilide tablet and at least one uncoated mexiletine pellet,
    wherein manufacturing said coated dofetilide tablet comprises geometrically mixing micronized dofetilide with starch, microcrystalline cellulose, colloidal silicon dioxide and magnesium stearate, yielding a dofetilide blend;
    compressing said dofetilide blend, yielding a dofetilide tablet; and
    coating said dofetilide tablet with polyvinyl alcohol polymeric film coating yielding a coated dofetilide tablet; and
    wherein manufacturing said uncoated mexiletine pellet comprises granulating mexiletine hydrochloride with the first microcrystalline cellulose and with the polyvinylpyrrolidone binder yielding a mexiletine granule;
    drying said mexiletine granule yielding a dry mexiletine granule;
    milling said dry mexiletine granule yielding a milled mexiletine granule;
    blending said milled mexiletine granule with the second microcrystalline cellulose, colloidal silicon dioxide and magnesium stearate yielding a mexiletine blend; and
    compressing said mexiletine blend yielding an uncoated mexiletine pellet; or
    (b) filling a gelatin capsule with at least one uncoated dofetilide tablet and at least one coated mexiletine pellet,
    wherein manufacturing said uncoated dofetilide tablet comprises geometrically mixing micronized dofetilide with starch, microcrystalline cellulose, colloidal silicon dioxide and magnesium stearate, yielding a dofetilide blend; and
    compressing said dofetilide blend, yielding an uncoated dofetilide tablet; and
    wherein manufacturing said coated mexiletine pellet comprises granulating mexiletine hydrochloride with the first microcrystalline cellulose and with the polyvinyl pyrrolidone binder yielding a mexiletine granule;
    drying said mexiletine granule yielding a dry mexiletine granule;
    milling said dry mexiletine granule yielding a milled mexiletine granule;
    blending said milled mexiletine granule with the second microcrystalline cellulose; colloidal silicon dioxide and magnesium stearate yielding a mexiletine blend;
    compressing said mexiletine blend yielding a mexiletine pellet; and coating said mexiletine pellet with polyvinyl alcohol polymeric film coating yielding a coated mexiletine pellet.

* * * * *